United States Patent [19]

Spiller

[11] 4,444,761

[45] Apr. 24, 1984

[54] CELLULOSE/CARBOXYMETHYL CELLULOSE MIXTURES USEFUL FOR CONTROLLING FECAL OUTPUT, AND METHODS EMPLOYING THEM

[75] Inventor: Gene A. Spiller, Los Altos, Calif.

[73] Assignee: Syntex (U.S.A.) Inc., Palo Alto, Calif.

[21] Appl. No.: 260,230

[22] Filed: May 4, 1981

[51] Int. Cl.³ ............................................. A61K 31/70
[52] U.S. Cl. ..................................................... 424/180
[58] Field of Search .............................................. 424/180

[56] References Cited

U.S. PATENT DOCUMENTS

| | | | |
|---|---|---|---|
| 3,440,065 | 4/1969 | La Via | 106/35 |
| 3,573,058 | 3/1971 | Tiemstra | 99/1 |
| 3,574,634 | 4/1971 | Singer | 99/83 |

FOREIGN PATENT DOCUMENTS 1094451  1/1981  Canada .

*Primary Examiner*—Frederick E. Waddell
*Attorney, Agent, or Firm*—Ellen J. Buckles; Tom M. Moran; Alan M. Krubiner

[57] ABSTRACT

Methods of controlling fecal output and of appetite control, and compositions therefor, employing a fiber-containing mixture of cellulose with CMC, are described.

16 Claims, No Drawings

CELLULOSE/CARBOXYMETHYL CELLULOSE MIXTURES USEFUL FOR CONTROLLING FECAL OUTPUT, AND METHODS EMPLOYING THEM

BACKGROUND OF THE INVENTION

Control of fecal output in human beings has become problematical with the increase in processed foods in the diet. The present invention concerns a fiber-containing bulking mixture to effect such control.

The proper function of the human large bowel (colon) depends greatly on the amount of plant fibers in the diet. Many minor disorders, as well as major diseases, may be due to lack of sufficient plant fiber intake, a typical situation in western European and American diets, which are high in animal products and refined carbohydrates. An excellent review of what is known at present about dietary fiber, and the requirements therefor, is *Fiber in Human Nutrition* edited by G. A. Spiller and R. J. Amen, Pleman Press, 1976.

In the context of "dietary fiber", the term "fiber" is somewhat misleading, because many substances normally classified in this category are not fiberous in the common sense of the word. Various alternate terms have been proposed; see for example, G. A. Spiller and E. A. Shipley "New Prospectives in Dietary Fiber", *Food Product Development*, pages 54–64, October 1976. For present purposes, and in agreement with most investigators, substances which will be termed "dietary fiber" include plant derived material, such as cellulose, pectin, lignin; and various gums and semi-synthetic materials such as, for example, carboxymethylcellulose, which are not digested before reaching the ileocecal valve, but which may possibly be digested by the colonic microflora.

The most common of the "minor disorders" resulting from a lack of dietary fiber is constipation, a problem that plagues a large portion of the population in industrial countries. Laxatives are in widespread use in western Europe and the United States, indicating the desire of people to relieve this condition. Of the laxatives presently known, the only truly physiological ones are the so-called bulk laxatives, which employ an agent which increases the volume of fecal matter in the large intestine by virtue of its own bulk and/or by virtue of its ability to absorb water. The most common ingredient in such preparations is an extract of psyllium seed. There are many disadvantages associated with this material, such as the requirement for the ingestion of substantial quantities to achieve the desired effect, a bulky stool that cannot be readily controlled or easily modified, tendencies of the extract to gel in solution in a short time, making for difficulty in oral ingestion, and problems with allergic reactions.

All natural extracts have the following disadvantages:

(a) They are subject to inconstant composition due to natural variation; this is clearly true of natural foodstuffs themselves. For example, in wheat bran, the amount of "fiber" present in the bran can vary tremendously depending on the milling process, that is, how much of the outer coating of the wheat is preserved. Even in unprocessed fruits and vegetables the composition is affected by degree of ripening and length of storage.

(b) They require dietary manipulation necessary to assure that the proper amount of "fiber" is ingested. This has the effect of forcing people to consume large amounts of certain foodstuffs which they may otherwise be unwilling to consume simply to obtain their fiber content.

The present invention offers a controllable and known mixture of pure materials, such that the proper amount of "fiber" intake can be carefully regulated. In addition, this preparation has properties which permit it to be included in foods normally consumed by the individual, as well as being palatable when taken alone.

It is known that a specified mixture of cellulose with the natural produce pectin can offer a controlled amount of fiber. See, for example, Belgian Patent 867,088, issued May 16, 1978.

The present invention relates to mixtures of cellulose and carboxymethylcellulose (CMC) useful for fecal output control, which are thus also antidiarrheal regulatory of colon function, and control appetite.

SUMMARY OF THE INVENTION

In one aspect, the invention concerns methods of controlling fecal output in a human subject and of controlling appetite, which method comprises administering orally to said subject, a daily dosage of between about 50 and 300 milligrams per kilogram body weight of a composition comprising or consisting essentially of purified cellulose and CMC in a weight ratio of between about 2:1 and 10:1.

In another aspect the invention concerns a dietary composition for controlling fecal output or for controlling appetite in a human subject which comprises or consists essentially of an effective amount of a mixture of purified cellulose and CMC in a relative weight ratio of between 2:1 and 10:1.

DETAILED DESCRIPTION OF THE INVENTION

The essence of the present invention is a composition comprising or consisting essentially of purified cellulose and purified carboxymethyl cellulose in a defined ratio as part of the regular dietary regimen.

The total quantity of mixture administered will, of course, depend to a large extent upon the particular subject involved. However, as a general rule between about 50 and 300, most preferably between about 85 and 225 milligrams per kilogram of body weight per day would be administered. For an average adult human subject of about 70 kilograms this would be between about 4 and 21, preferably between about 6 and 16 grams per day. The dietary composition containing the cellulose/CMC mixture may be administered in unit or divided daily dosages, for example, entirely with one meal, or portionwise, for example, with each meal.

Of course, the particular effect on any given subject will depend to a certain extend upon the total dietary composition, so that the method achieves more predictable and reproduceable results when the said cellulose/CMC composition is substantially the sole source of dietary fiber. If the diet includes a substantial amount of one or more fiber components in addition to that being administered in accordance with the method herein, the beneficial effects of the subject method may be altered. However, one major advantage of the present invention is the avoidance of dietary manipulation to insure the proper amount and proper mix of fiber in the diet.

The cellulose/CMC composition as described above may be administered by itself, for example by suspension in water (with optional addition of a flavoring agent) or may be combined with other dietary components such as protein sources, lipids, carbohydrates, vitamins, minerals, and the like. The cellulose/CMC mixture can be utilized as a convenient pre-mix for the preparation of baked goods such as breads, cakes, cookies, muffins, and the like. It may also be combined into other foods, for example, hamburger, casseroles or puddings and beverages, or it may be conveniently used as a sprinkle-on additive to prepared foods. It may also be combined with carbohydrate material, commonly sucrose, to form granules, which may be simply swallowed as is, washed down with water, or dispersed in water.

The cellulose/CMC mixture has good dispersability and suspension stability, is moderately soluble in water at room temperature, and has an acceptable viscosity. It is also acceptable in terms of flavor, odor, mouth feel and appearance. In terms of the above properties, the subject composition is superior to either cellulose or CMC alone.

Cellulose utilized for the present composition and method should be of high purity, at least 90 percent, and is preferably utilized as a finely divided powder or crystalline form of between about 20 and 140 microns, most preferably between about 50 and 60 microns. Examples of commercially available purified cellulose are Solka Floc (product of Brown Company) and Avicel (product of FMC Corporation).

CMC used for the present method and composition must also be highly purified; however commercially available CMC is of sufficient purity to satisfy this requirement.

The subject mixtures may be prepared by any of the normal procedures for blending solid components of this type intended for oral human consumption, for example, a household blender or shaker, or by simple stirring, for example, in a glass with a spoon.

PREFERRED EMBODIMENTS

Biologically effective mixtures consisting essentially of cellulose and carboxymethyl cellulose can be prepared in the range of about 2:1 to 10:1, cellulose to CMC ratio. However, in terms of acceptability in taste and of compatibility with other ingredients, it is preferred that the ratio be between 5:1 and 9:1, cellulose to CMC; most preferably 7:1, cellulose/CMC.

The composition can be administered in amounts within the range of 50 to 300 milligrams per kilogram of body per day, however, it is preferred that this range be between 85 and 225 milligrams per kilogram of body weight.

If the composition is to be used for controlling fecal output, any of the modes of administration described herein is satisfactory as a suspension, of a powdered or granule form, included in recipes for ordinary foods, chewable or swallowable granules, etc. However, if it is to be used for appetite control, it is preferable that the composition be administered as granules or as a suspension, about 0.5 hours to 1 hour before meals.

A more complete appreciation of the methods and compositions of the present invention may be had by reference to the following specific examples. These examples are illustrative only and should not be construed as limitative of the scope or spirit of the present invention.

EXAMPLE 1

Preparation of Purified Cellulose-CMC Mixtures for Administration

Purified Cellulose—99.5% cellulose, essentially free of lignin, food grade, 50–60μ (Solka-Floc BW 40, product of Brown Company).

CMC—commercial grade CMC is obtained from Hercules Powder Company.

A powder mixture of the cellulose/CMC is prepared as follows:

87.5 g. of purified cellulose and 12.5 g. of CMC are mixed in a Patterson Kelly (P-K) liquid solid blender until well blended (about eight minutes).

When a flavored powder is desired, the following procedure is utilized (illustrated for lemon flavor):

0.3 g. of natural lemon flavor and 0.8 g. of citric acid are mixed well and 24.0 g. of powdered sucrose (with 3% cornstarch) is added and mixed in a P-K blender until well blended (about eight minutes).

The above mixture is added to 20 g. of the above described fiber mixture and mixed in a P-K blender until well blended (about 15 minutes).

EXAMPLE 2

Illustrative Recipes Incorporating the Composition as a Premix

Quiche Lorraine: 5 g. Cellulose/CMC/Serving

308 Calories/Serving 537 mg/Serving

½ lb. bacon, chopped into 1 inch pieces, cooked and drained 2 large eggs

¼ tsp. salt

¼ tsp. dry onion

¼ tsp. nutmeg 1 cup milk

½ cup cellulose/CMC 1 cup grated Cheddar cheese 1 9" frozen pie crust

Beat eggs, salt, onion and nutmeg. Add milk, then cellulose/CMC. Beat well. Place bacon, then cheese, then egg mixture into crust. Bake at 375° F. for 40 min. or until brown. Makes 6 servings.

Asparagus-Cauliflower Au Gratin 5 g Cellulose/CMC/Serving 384 Calories/Serving 10 oz. asparagus—cooked and drained 10 oz. cauliflower—cooked and drained 2 cups grated cheddar cheese 1 can cream of celery soup ½ cup milk ¼ tsp. dry mustard 2 tbsp. margarine ⅓ cup cellulose/CMC Blend cheese, soup, milk, mustard and margarine. Stir in cellulose/CMC. Place vegetables in baking dish. Pour cheese mixture over them. Bake at 325° for 25 min. Makes 4 servings.

Sloppy Joes: 541 Calories/Serving 10 g Cellulose/CMC 1 lb. ground beef 4 tbsp. chopped green pepper 4 tsp. dry onion 1 tsp. salt 4 cups tomato sauce ⅜ cup cellulose/CMC Brown meat, pepper and onion. Mix tomato sauce, salt, and cellulose/CMC. Add to meat mixture and heat until bubbly. Serve on hamburger rolls. Serves 4.

Pizza (Deep Dish):

240 Calories/Serving 17.5 g Cellulose/Serving
1 pkg. Appian Way Pizza Mix-Regular
¾ cup warm water
⅓ cup cellulose/CMC
½ cup chopped green pepper
2 tsp. dry onion
2 cups grated mozzarella cheese
4 oz. can whole peeled tomatoes w/sauce-diced
¼ cup cellulose/CMC Combine, water, dough mix, and ⅓ cup cellulose/CMC. Placed in greaded 9"×9" sq. pan. Bake crust at 425° for 10 min.

Combine topping mix, ¼ cup cellulose/CMC, and tomatoes. Spread on cooked crust. Sprinkle cheese, onions, and green pepper over sauce. Bake at 425° for 15 min. Makes 2 servings.

Oatmeal-Applesauce Cookies: 100 Calories/Cookie 1.5 g Cellulose/CMC/Cookie 153 mg/Serving
7 tbsp. margarine
¾ cup brown sugar
1 egg
¼ cup applesauce
1 cup flour
¾ tsp. baking soda
1 tsp. baking powder
¼ tsp. salt
2 tsp. cinnamon
2 tsp. nutmeg
½ cup cellulose/CMC
½ cup oatmeal
½ cup raisins Cream together margarine and sugar. Add egg and applesause. Sift together dry ingredients. Add to creamed mixture. Stir in cellulose/CMC, then oats, then raisins. Place by teaspoonsful onto greased cookie sheet. Bake at 375° F. for 25 minutes. Makes 20 large cookies.

EXAMPLE 3

Comparison of Physical and Organoleptic Properties of Cellulose/CMC Compositions

| Property | CMC | Purified Cellulose | Purified Cellulose CMC Mixture (7:1) |
|---|---|---|---|
| Physical | | | |
| Dispersability | poor | good | good |
| Suspension stability | good | poor-clear serum in ½ hour | good |
| Solubility | soluble | Insoluble | Partially soluble |
| Viscosity | Judged unacceptably high | Low, acceptable | Acceptable |
| Organoleptic | | | |
| Flavor | Bland | Bland | Acceptable |
| Odor | Acceptable | Acceptable | Acceptable |
| Mouthfeel | Mucilagenous but acceptable | Chalky, mealy | Acceptable |
| Appearance | Translucent solution | Suspension of white particles | Milky-white solution |

Evaluations are based on solutions equivalent to 20 g. fiber in 10 oz. water (6.7% solution)

EXAMPLE 4

Granule Formulation

The following formulation results in sugar coated granules which can be simply popped into the mouth like candy, and either swallowed as such, or washed down with water or juice.

A sugar syrup is made by dissolving 25% to 50% by weight of sucrose in water. About 100 g of the cellulose:CMC mixture (7:1) as prepared in Example 1 is dissolved in a minimum quantity of syrup—about 100 g mixture to 30 g syrup.

The mixture is then placed in appropriate granulating equipment, such as a coating pan or a disc pelletizer. The resulting granules contains about 15% sugar (after the water has evaporated).

The granules may also be compressed into wafers or tablets, of varying sizes, e.g., 2 grams.

EXAMPLE 5

Efficacy Studies of the Cellulose/CMC Composition

Protocol:

Forty human subjects were divided into 5 groups of 8 subjects each. All subjects were required to eat a low residue diet prepared by the diet kitchen throughout a 20-day period wherein calories were adjusted to maintain the weight of each subject. In addition, as part of the total dietary intake, each subject received one of the five compositions listed in the results chart below. Each subject received one of these compositions for the first 10 days, and another of these compositions for the second 10 days. Fecal collections were made only on each of the last 5 days of each 10 day test period. Results were measured in terms of average fecal wet weight (g/day) and of transit time (days). Transit time was measured by the method of Hinton J. M. et al, Gut, Vol. 10, 842 (1969).

The cellulose/pectin composition listed below and used for comparison was a mixture of 70 g cellulose to 30 g pectin flavored with lemon extract, prepared essentially in the manner described for the cellulose/CMC mixtures in Example 1. The cellulose/CMC mixtures were prepared as described in Example 1, using the lemon flavored alternative.

Results:

Stools were collected from each of the subjects, on the last 5 days of each 10 day period, as indicated above. The following average results were obtained:

| Composition | Amount | Average Fecal Wt. (g/day) | Transit Time (Days) |
|---|---|---|---|
| Sucrose | 10.7 g/day | 64.8 | 4.3 |
| Cellulose/Pectin | 18 g/day | 114.5 | 3.1 |
| Cellulose/CMC | 16 g/day | 110.5 | 3.3 |
| Cellulose/CMC | 10.7 g/day | 106.9 | 3.3 |
| Cellulose/CMC | 5.3 g/day | 89.2 | 3.2 |

We claim:

1. A method for controlling fecal output in a human subject, which method comprises administering orally to said subject a daily dosage of between about 50 and 300 milligrams of a mixture of purified cellulose and carboxymethylcellulose (CMC) in a weight ratio of between about 2:1 and 10:1; cellulose:CMC, per kilogram body weight.

2. The method of claim 1 wherein said weight ratio of cellulose to CMC is between about 5:1 and 9:1; cellulose:CMC.

3. The method of claim 1 wherein said weight ratio of cellulose to CMC is about 7:1; cellulose:CMC.

4. The method of claim 1 wherein the daily dosage is between about 85 and 225 mg per kg body weight.

5. A method of controlling fecal output in a human subject, which method consists essentially of administering orally to said subject a daily dosage of between about 50 and 300 milligrams of a mixture of purified cellulose and CMC in a weight ratio of between about 2:1 and 10.1; cellulose:CMC, per kilogram body weight.

6. The method of claim 5 wherein said weight ratio of cellulose to CMC is between about 5:1 and 9:1; cellulose:CMC.

7. The method of claim 5 wherein said weight ratio of cellulose to CMC is about 7:1; cellulose:CMC.

8. The method of claim 5 wherein the daily dosage is between about 85 and 225 mg per kg body weight.

9. A method of controlling appetite in a human subject, which method comprises administering orally to said subject a daily dosage of between about 50 and 300 milligrams of a mixture of purified cellulose and CMC in a weight ratio of between about 2:1 and 10:1; cellulose:CMC, per kilogram body weight.

10. The method of claim 9 wherein said weight ratio of cellulose to CMC is between about 5:1 and 9:1; cellulose:CMC.

11. The method of claim 9 wherein said weight ratio of cellulose to CMC is about 7:1; cellulose:CMC.

12. The method of claim 9 wherein the daily dosage is between 85 and 225 mg per kg body weight.

13. A method of controlling appetite in a human subject, which method consists essentially of administering orally to said subject a daily dosage of between about 50 and 300 milligrams of a mixture of purified cellulose and CMC in a weight ratio of between about 2:1 and 10.1; cellulose:CMC, per kilogram body weight.

14. The method of claim 13 wherein said weight ratio of cellulose to CMC is between about 5:1 and 9:1; cellulose:CMC.

15. The method of claim 13 wherein said weight ratio of cellulose to CMC is about 7:1; cellulose:CMC.

16. The method of claim 13 wherein the daily dosage is between 85 and 225 mg per kg body weight.

* * * * *